(12) United States Patent
Clements et al.

(10) Patent No.: US 10,565,793 B2
(45) Date of Patent: Feb. 18, 2020

(54) VIRTUAL REALITY SERVICES WITHIN CONTROLLED-ENVIRONMENT FACILITY

(71) Applicant: SECURUS TECHNOLOGIES, INC., Dallas, TX (US)

(72) Inventors: Alice J. Clements, Coppell, TX (US); Scott Passe, Forney, TX (US); Luke Keiser, Frisco, TX (US)

(73) Assignee: Securus Technologies, Inc., Carrollton, TX (US)

( * ) Notice: Subject to any disclaimer, the term of this patent is extended or adjusted under 35 U.S.C. 154(b) by 1 day.

(21) Appl. No.: 15/440,273

(22) Filed: Feb. 23, 2017

(65) Prior Publication Data

US 2018/0240275 A1    Aug. 23, 2018

(51) Int. Cl.
*G09G 5/00* (2006.01)
*G06T 19/00* (2011.01)
*G06Q 50/26* (2012.01)

(52) U.S. Cl.
CPC ........... *G06T 19/006* (2013.01); *G06Q 50/26* (2013.01)

(58) Field of Classification Search
CPC ....... G06T 19/006; G06T 19/00; G06F 3/011; G06F 3/012; G02B 27/017
USPC ........................................................ 345/633
See application file for complete search history.

(56) References Cited

U.S. PATENT DOCUMENTS

| | | | | |
|---|---|---|---|---|
| 2002/0168621 A1* | 11/2002 | Cook | ....................... | G09B 7/00 434/350 |
| 2008/0143538 A1* | 6/2008 | Young | ................ | G08B 21/0423 340/573.1 |
| 2012/0262271 A1* | 10/2012 | Torgersrud | .............. | G06F 21/32 340/5.53 |
| 2018/0219950 A1* | 8/2018 | Hodge | .................. | H04L 67/141 |

* cited by examiner

*Primary Examiner* — Gordon G Liu
(74) *Attorney, Agent, or Firm* — Fogarty LLP

(57) ABSTRACT

Embodiments provide methods and systems for regulating the use of virtual reality environments provided to residents of controlled-environment facilities. In response to a request for virtual reality programs from an inmate, the privilege status of the inmate is used to determine the available virtual environments in which the inmate may participate. The participation of the inmate within a virtual reality session may be restricted based on the privilege status of the inmate. Any limitations on an inmate's participation within an approved virtual environment may be enforced by restricting the behavior of an avatar representing the inmate within the virtual environment. The privilege status of inmates may be used to enforce restrictions that prohibit contact between certain inmates or certain classifications of inmates. The participation of inmates may be restricted and terminated based on a measured physiological responses to the inmate's participation in a virtual environment.

30 Claims, 4 Drawing Sheets

VIRTUAL REALITY SERVICES WITHIN CONTROLLED-ENVIRONMENT FACILITY

TECHNICAL FIELD

The following description relates generally to providing virtual reality services to residents of a controlled-environment facility, and more particularly to enforcing restrictions on the virtual reality services provided to residents of a controlled-environment facility.

BACKGROUND OF THE INVENTION

According to the International Centre for Prison Studies, the United States has the largest prison population in the world. By current estimates, over two million inmates are incarcerated in U.S. prisons. In general, inmates that have been convicted of felony offenses serve longer sentences in prisons (e.g., federal or state prisons), whereas inmates that have been convicted of misdemeanors receive shorter sentences that are typically served in jails (e.g., county jail). In addition, upon being detained by authorities, an inmate may serve significant periods of time incarcerated in a local jail while awaiting release on bond and, in some cases, while awaiting trial. During all of these periods of incarceration, an inmate may have opportunities to communicate with the outside world.

By allowing inmates to communicate with friends and family while incarcerated, the justice system aims to facilitate their transition back into society upon release. Traditional visitation sessions provided by controlled-environment facilities include telephone calls and in-person visits. More recently, technological advances and the proliferation of affordable mobile devices enabling various forms of communication have allowed controlled-environment facilities to provide other types of visitation sessions, including video conferences, email and online chat sessions. As these advances have continued, the use of virtual reality is becoming more commonplace.

Virtual reality allows a user to view, and to some extent interact with, a virtual three-dimensional environment generated through the execution of a virtual reality software program and displayed to the user via a specially configured headset. The virtual reality programs may support more than one user participating in virtual reality session, in which case each participant or portion of that participant may be represented within the virtual environment via an avatar. A resident of a controlled-environment facility may be subject to various restrictions with regard to personal behavior and communicating with other residents and visitors. In certain scenarios, it may be necessary to apply such restrictions to a resident's participation in virtual reality sessions.

BRIEF SUMMARY

Certain embodiments provide a method for regulating the use of a plurality of supported virtual reality environments by a plurality of residents of a controlled-environment facility. The method includes receiving a request for a virtual reality session by a first resident of the plurality of residents of the controlled-environment facility; determining one or more privilege status restrictions pertaining to the first resident; determining, based on the privilege status restrictions, a list of virtual reality environments of the plurality of supported virtual reality environments that are allowed for the first resident, wherein the privilege status restrictions restrict the inmate from certain of the plurality of supported virtual reality environments; receiving a selection of a virtual reality environment from the first resident, wherein the selection is made by the resident from the list of allowed virtual reality environments; inserting an avatar representing the first resident into the selected virtual reality environment, wherein the avatar is controlled within the selected virtual reality environment by the resident; and restricting the behavior of the avatar based on the determined privilege status restrictions.

In certain additional embodiments of the method, the privilege status restrictions are based on the resident's behavior in the controlled-environment facility. In certain additional embodiments of the method, the list of available virtual reality environments includes a first virtual reality environment that is currently hosting a second resident of the plurality of residents. In certain additional embodiments of the method, the determined privilege status restrictions prohibit the first resident from joining the first virtual reality environment based on the first virtual reality environment hosting the second resident. In certain additional embodiments of the method, the determined privilege status restrictions prohibit the first resident from participating in virtual reality environments with other residents of the plurality of residents. In certain additional embodiments, the method also includes monitoring one or more physiological responses of the resident while the resident is controlling the avatar in the selected virtual reality environment. In certain additional embodiments, the method also includes assessing the first resident by comparing the one or more physiological responses of the resident to prior physiological responses captured during prior participation of the first resident in the selected virtual reality environment. In certain additional embodiments, the method also includes warning the resident if a physiological response of the one or more physiological responses exceeds a specified threshold. In certain additional embodiments of the method, the specified threshold is determined based on the determined privilege status of the first resident.

Certain embodiments provide a system for regulating the use of a plurality of supported virtual reality environments by a plurality of residents of a controlled-environment facility. The system includes a virtual reality access point configured to receive a request for a virtual reality session by a first resident of the plurality of residents of the controlled-environment facility and further configured to receive a selected virtual reality environment from the first resident, wherein the selection is made by the resident from a list of allowed virtual reality environments. The system further includes a virtual reality control system configured to determine one or more privilege status restrictions pertaining to the first resident and further configured to determine, based on the privilege status restrictions, the list of virtual reality environments of the plurality of supported virtual reality environments that are allowed for the first resident, wherein the privilege status restrictions restrict the inmate from certain of the plurality of supported virtual reality environments. The system further includes a virtual reality server configured to insert an avatar representing the first resident into the selected virtual reality environment, wherein the avatar is controlled within the selected virtual reality environment by the resident and further configured to restrict the behavior of the avatar based on the determined privilege status restrictions.

In certain additional embodiments of the system, the privilege status restrictions are based on the resident's behavior in the controlled-environment facility. In certain additional embodiments of the system, the list of available virtual reality environments includes a first virtual reality environment that is currently hosting a second resident of the plurality of residents. In certain additional embodiments of the system, the determined privilege status restrictions prohibit the first resident from joining the first virtual reality environment based on the first virtual reality environment hosting the second resident. In certain additional embodiments of the system, the determined privilege status restrictions prohibit the first resident from participating in virtual reality environments with other residents of the plurality of residents. In certain additional embodiments of the system, the access point is further configured to received inputs from one or more sensors configured to monitor one or more physiological responses of the resident while the resident is controlling the avatar in the selected virtual reality environment. In certain additional embodiments of the system, the virtual reality control system is further configured to assess the first resident by comparing the one or more physiological responses of the resident to prior physiological responses captured during prior participation of the first resident in the selected virtual reality environment. In certain additional embodiments of the system, the virtual reality control system is further configured to warn the resident if a physiological response of the one or more physiological responses exceeds a specified threshold. In certain additional embodiments of the system, the specified threshold is determined based on the determined privilege status of the first resident.

Certain embodiments provide a method for a virtual reality visitation between a resident of a controlled-environment facility and a visitor, the method comprising: receiving a request for the virtual reality visitation session by the first resident; determining one or more privilege status restrictions pertaining to the first resident; determining, based on the privilege status restrictions, a list of virtual visitation environments that are allowed for the first resident; receiving a selection of a virtual visitation environment from the first resident, wherein the selection is made by the resident from the list of allowed virtual visitation environments; inserting an resident avatar representing the first resident into the selected virtual visitation environment, wherein the resident avatar is controlled within the selected virtual visitation environment by the resident; inserting an visitor avatar representing the visitor into the selected virtual visitation environment, wherein the visitor avatar is controlled within the selected virtual visitation environment by the visitor; and restricting the behavior of the avatar in the virtual visitation environment based on the determined privilege status restrictions. In certain additional embodiments of the method, the privilege status restrictions are based on the resident's behavior in the controlled-environment facility.

BRIEF DESCRIPTION OF THE DRAWINGS

Figure 1:
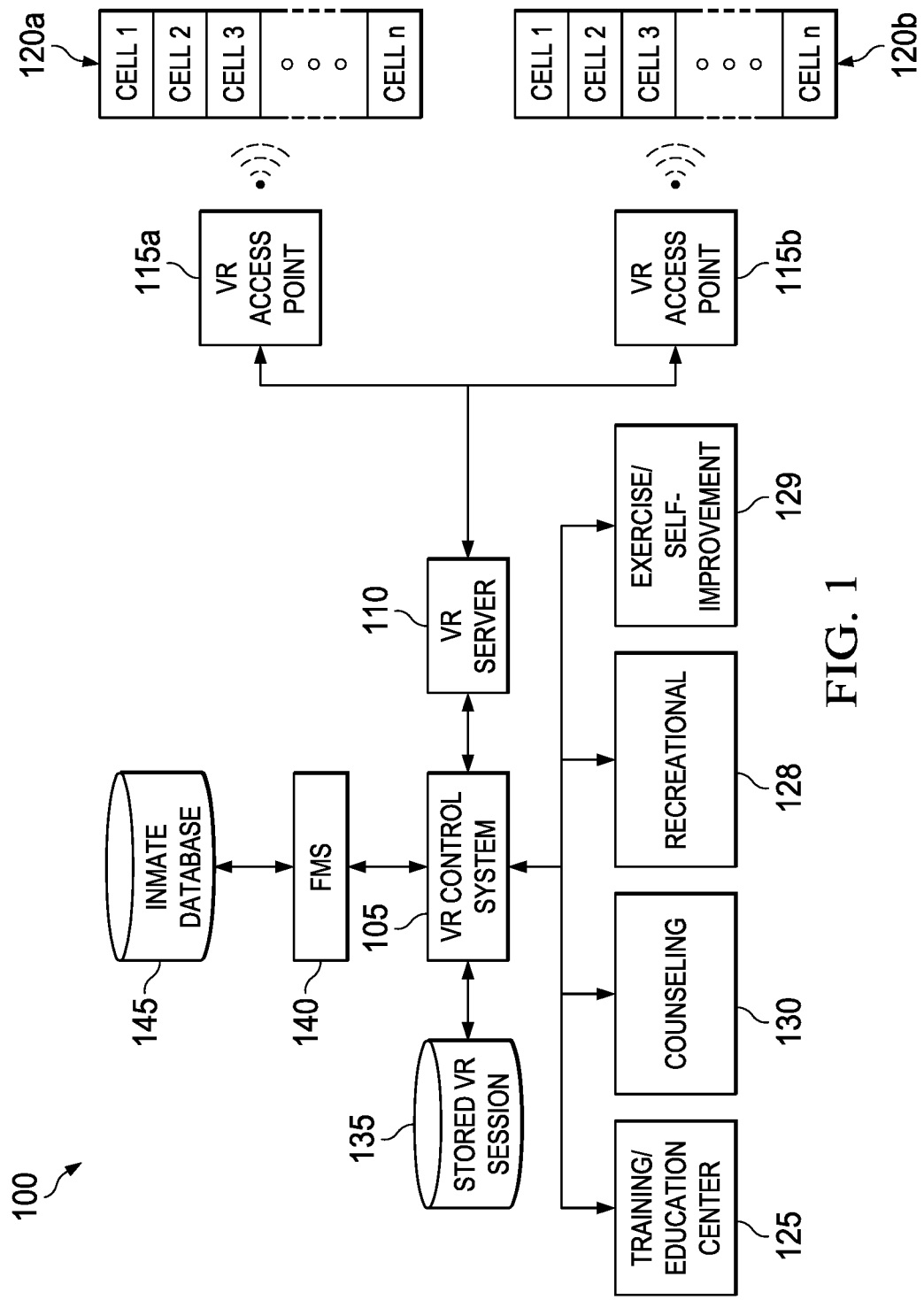

Having thus described the invention in general terms, reference will now be made to the accompanying drawings, which are not necessarily drawn to scale, and wherein:

FIG. 1 is a diagram illustrating certain components of a system for providing residents of a controlled environment facility with virtual reality services according to various embodiments.

Figure 2:
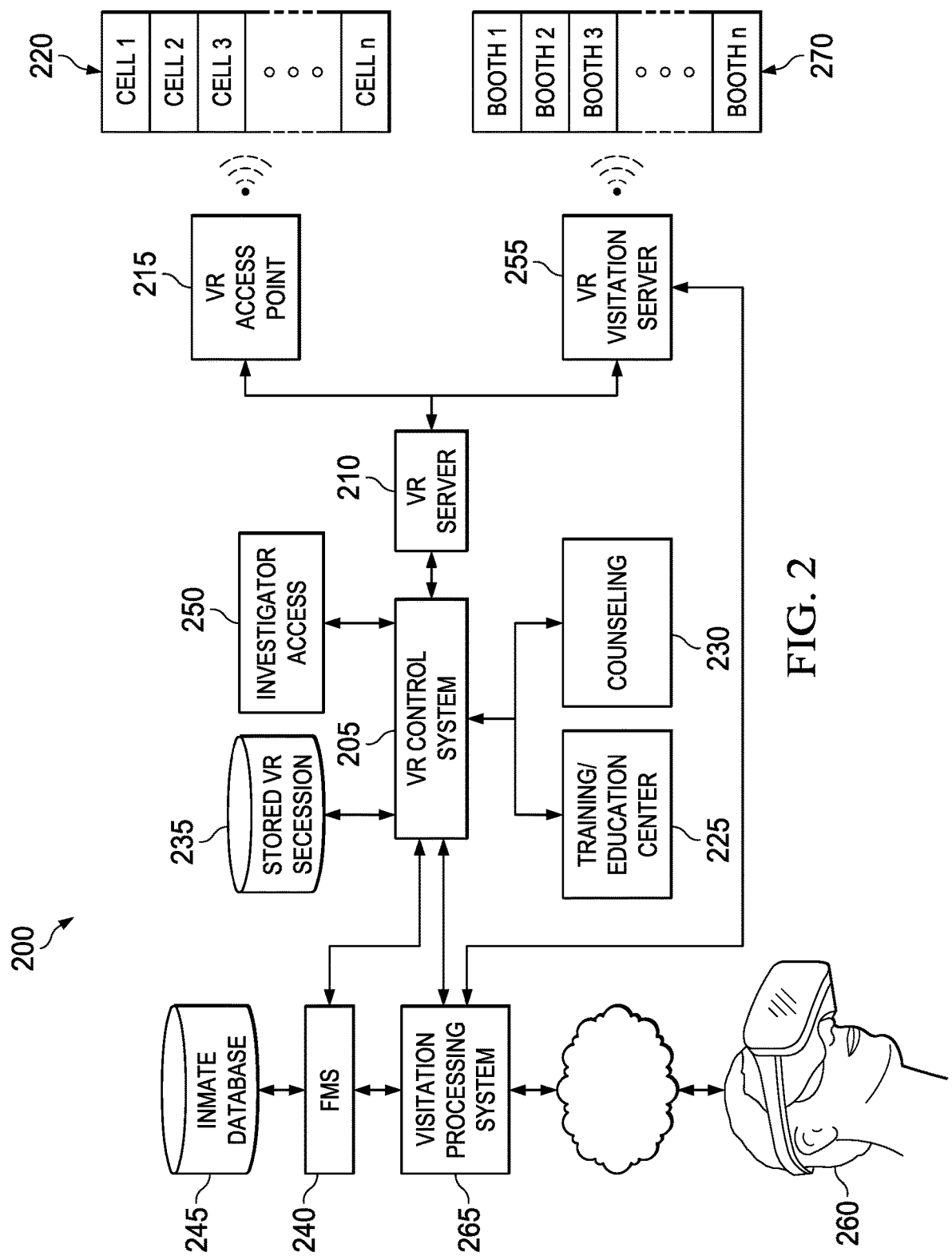

FIG. 2 is a diagram illustrating certain additional components of a system for providing residents of a controlled environment facility with virtual reality visitation services according to various embodiments.

Figure 3:
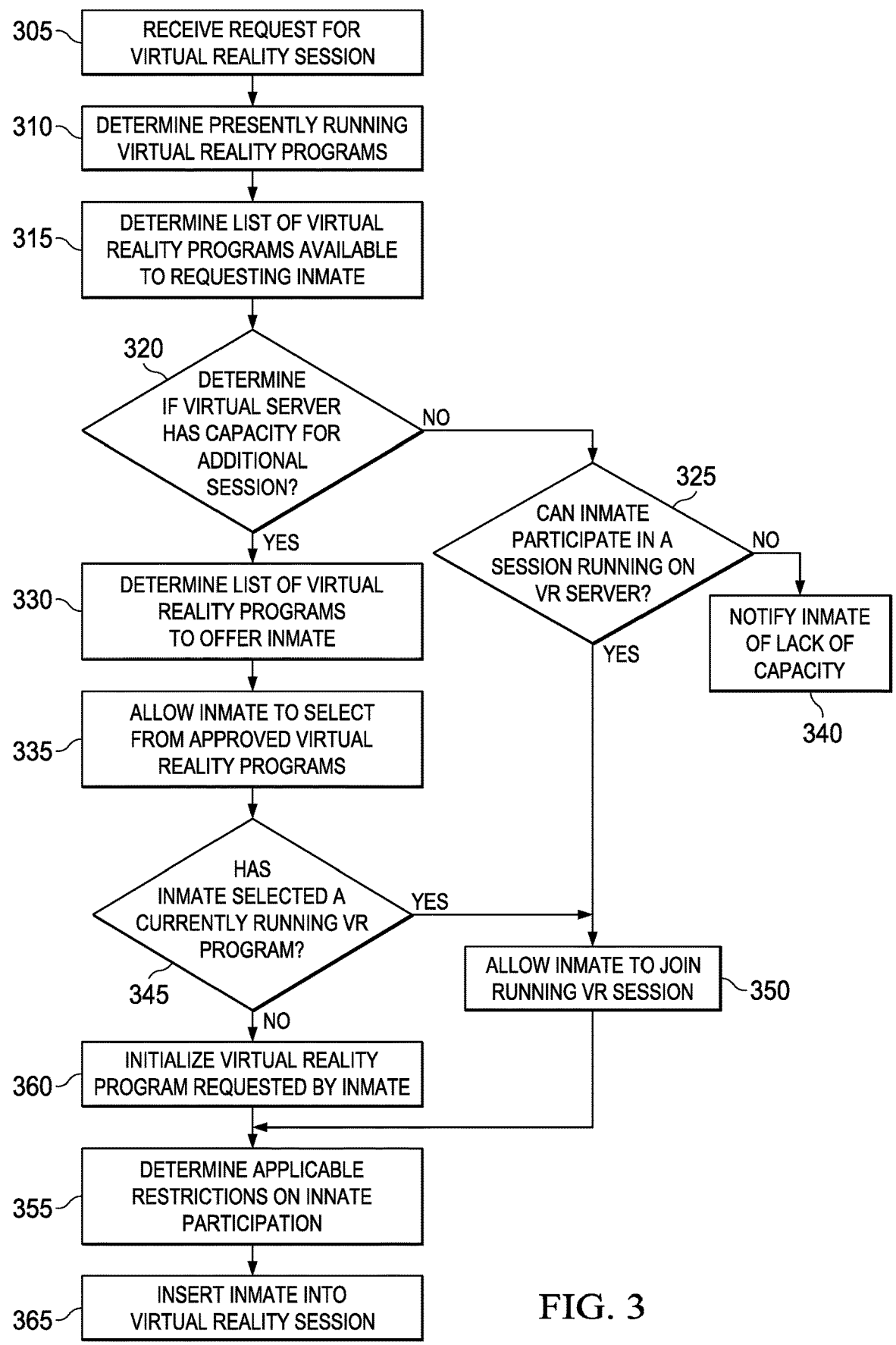

FIG. 3 is a flowchart diagram illustrating certain steps of process according to various embodiments for providing a resident of a controlled environment facility with a virtual reality service.

Figure 4:
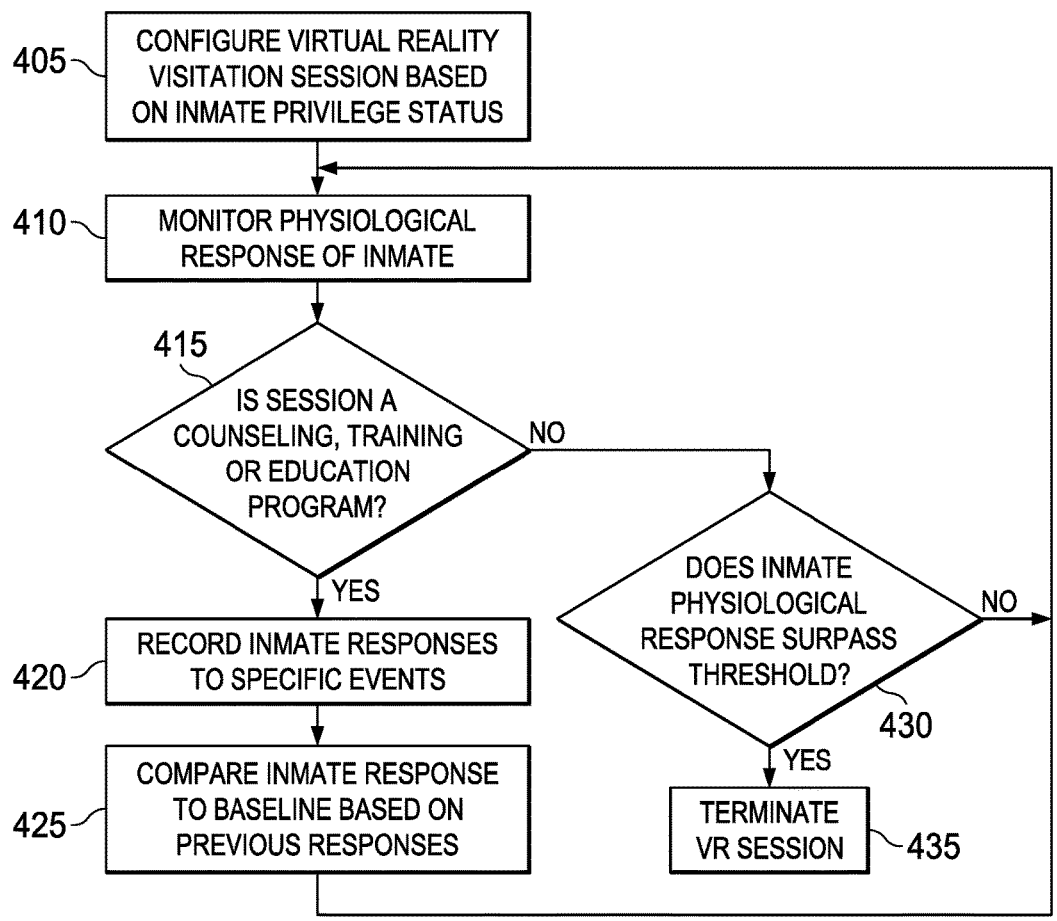

FIG. 4 is a flowchart diagram illustrating certain steps of another process according to various embodiments for disconnecting a resident of a controlled environment facility from a virtual reality session based on various conditions.

Figure 5:
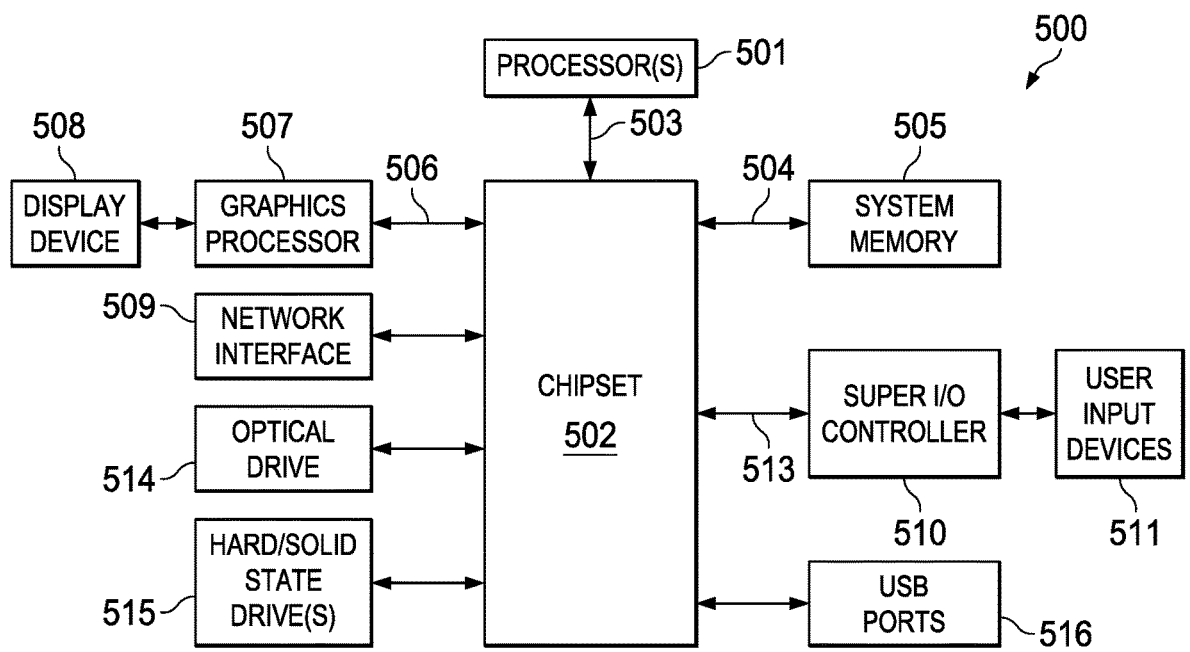

FIG. 5 is diagram illustrating certain components of a system for providing residents of a controlled environment facility with virtual reality services according to various embodiments.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

For example, various types of controlled-environment facilities are present in today's society, and persons may be voluntary or involuntary residents of such facilities, whether temporarily or permanently. Examples of controlled-environment facilities may include correctional institutions (e.g., municipal jails, county jails, state prisons, federal prisons, military stockades, juvenile facilities, detention camps, home incarceration environments, etc.), certain healthcare facilities (e.g., certain hospitals and nursing homes, certain mental health facilities, certain rehabilitation facilities, such as drug and alcohol rehabilitation facilities, etc.), certain restricted living quarters (e.g., barracks, certain dormitories, etc.), and the like. For convenience of explanation, various examples discussed herein are presented in the context of correctional facilities, or the like. For instance, in some of the embodiments discussed below, a controlled-environment facility may be referred to as a correctional facility, jail or prison, and its residents may be referred to as inmates, arrestees, or detainees. It should be understood, however, that the systems and methods described herein may be similarly applicable to other types of controlled environment facilities and their respective residents (e.g., a hospital and its patients, a school dormitory and its students, etc.).

FIG. 1 is a diagram illustrating certain components of a virtual reality system 100 provided within a controlled environment facility according to various embodiments. The embodiment illustrated in FIG. 1 provides residents of a controlled environment facility with various virtual reality services such as training and education programs 125, counseling services 130, recreational activities 128 and physical/self-improvement routines 129. In a controlled environment facility, residents are typically restricted with regards to their actions and movements within the different areas of the facility. For instance, in a correctional facility, all movements by inmates are heavily restricted. Inmates are allowed out of their cells and into common areas according to strict schedules and rules that prohibit many personal actions with regard to physical altercations, possession of contraband items, allowed interactions with staff, predatory behavior against other inmates, etc. Providing virtual reality services to an inmate of a correctional facility may require enforcing certain of these same restrictions on the inmate's participation within the provided virtual environments.

Inmates held within a correctional facility may be categorized and managed based on various criteria in order to ease administration of the inmate population. For instance, an inmate may be categorized based on any known gang affiliations by the inmate. Such types of information may be used to ensure that an inmate is kept isolated from inmates affiliated with rival gangs and may be likewise used to keep inmates isolated from suspected co-conspirators within the inmate's known or suspected gang. In other scenarios, inmates that have been convicted of certain crimes may be segregated from the general population of inmates. Inmates with certain medical issues may be managed as a group in order to facilitate various treatment regimens, such as drug and alcohol addiction counseling.

Another categorization of inmates may be according to the privilege status of the inmate. The privilege status of an inmate may be determined based in part on the inmate's conformance with the rules and regulation of the correctional system. At one end of the privilege status spectrum, inmates with a history of violent behavior may be housed within a high-security portion of a facility where inmates are kept in isolation. Such inmates have few privileges. Inmates in the general population generally have allotted privileges with regard to visitation allowances, freedom of movement with other inmates in common areas, allowed recreational and educational activities, etc. In certain settings, certain inmates may be designated by categories such as "trustees" that grant additional privileges based on an established history of good behavior by the inmate. Such inmates may be granted additional visitations, opportunities to participate in work programs, additional educational programs, greater freedom of movement, etc.

In the system of FIG. 1, virtual reality services are provided to inmates at a correctional facility where the inmates are housed in cells 120*a-b*. In the illustrated embodiment, the cells are organized into two groups 120*a* and 120*b*. Other embodiments may organize and house inmates in any number of different groups. Each group 120*a-b* may contain any number of cells, may each house any number of inmates and may be physically organized into various layouts such as cell blocks, wings, pods, units, etc. In certain embodiments, groups of cells may house inmates with a similar privilege status categorization. For instance, one group of cells 120*a* may house violent inmates within a high-security portion of a correctional facility, with these high-security inmates receiving fewer privileges than general population of inmates that are housed in another group of cells 120*b*.

The virtual reality services are provided to inmates utilizing a virtual reality control system 105 according to various embodiments. The virtual reality control system 105 is used to provide inmates with controlled access to the virtual reality services according to the rules and procedures implemented by a controlled environment facility. In the illustrated embodiment, the virtual reality control system 105 is configured to provide inmates 120*a-b* with virtual reality training and education services 125 and virtual reality counseling services 130. Other embodiments may provide inmates with additional or different virtual reality services such as recreational and entertainment programs. For instance, certain embodiments may provide inmates with virtual reality recreational activities 128, such as games, entertainment programing and social media scenarios that may allow various levels of interaction without non-inmate participants. Certain embodiments may provide inmates with virtual reality exercise and self-improvement routines 129, such as physical fitness, yoga, meditation, or other activities, that may be provided to inmates with relatively few restrictions.

In some embodiments, the virtual reality control system 105 may be co-located within a controlled-environment facility. For instance, the virtual reality control system 105 may be located within a correctional facility that houses the two groups of inmates 120*a* and 120*b*. In other embodiments, the virtual reality control system 105 may be centrally and/or remotely located with respect to one or more controlled environment facilities. Whether co-located or located remotely from a controlled environment facility, virtual reality control system 105 may be used to provide virtual reality services to inmates of multiple controlled-environment facilities. For instance, in certain embodiments, the virtual reality control system 105 may be centrally located and the inmates in group 120*a* and the inmates in group 120*b* are located in different controlled environment facilities.

In such embodiments, a centrally controlled virtual reality control system 105 may provide virtual reality services to inmates 120*a* at one controlled-environment facility and to inmates 120*b* at another controlled-environment facility. In certain scenarios, the virtual reality control system 105 may be configured to strictly prohibit any virtual reality interactions between the two groups of inmates 120*a* and 120*b* from the two facilities. In other scenarios, the virtual reality control system 105 may allow limited interactions between inmates from different facilities. For instance, additional privilege status restrictions may be enforced for participating in virtual reality sessions with inmates housed at different facilities. In certain embodiments, virtual reality services may be provided to inmates by two different virtual reality systems that each provide virtual reality services to one of the facilities. In such embodiments, the virtual reality systems may exchange privilege status information regarding the inmates in order to enforce appropriate restrictions on a virtual reality session that is hosted by one of the two systems.

In certain embodiments, inmates in each of the groups 120*a-b* may utilize a virtual reality headset to access the virtual reality services provided by the virtual reality control system 105 via the virtual reality server 110. A virtual reality headset may be provided to an inmate on a temporary or permanent basis. In certain scenarios, an inmate may own the virtual reality headset and may be allowed to maintain possession of the headset. In the certain embodiments, the virtual reality headsets utilized by inmates may include one or more visual display elements that provide the inmate with three-dimensional vision within virtual reality environments. The visual display element may be a special purpose display interface that is integrated into the headset. Instead, the visual display element may be a multi-purpose display interface that is temporarily coupled to the headset in order to participate in a virtual reality session. In certain embodiments, the headset also provides audio in the form of integrated headphones. In certain embodiments, the headset also includes an integrated microphone that allows the inmate to provide audio input during the virtual reality session. Various other configurations of virtual reality headsets may be utilized.

In various embodiments, various different sensors may be integrated into the virtual reality headset. Such sensors may be used to detect positional and movement information, such as the orientation of the user and the direction of the user's gaze. Sensors integrated into the headset may collect information regarding movement of the user, such as hand movements and facial gestures. In certain embodiments, sensors may be located within the individual cells 120a-b in order to capture inmate movement information. In certain embodiments, inmates may be allowed to attach various wearable sensors that may be used to collect additional movement information.

In certain embodiments, the virtual reality headsets may be configured to require authentication of an inmate. For instance, an inmate may be required to enter a PIN (Personal Identification Number) and/or password before being allowed to access any virtual reality sessions hosted by the virtual reality server 110. In certain embodiments, an inmate may be required to provide biometric verification, such as a voice print, fingerprint or other biometric indicator in order to participate in provided virtual reality services. Upon being authenticated, the inmate may be provided with a list of available virtual reality services.

In certain embodiments, the virtual reality access points 115a-b may provide the virtual reality server 110 with the identity of the authenticated user and the virtual reality server 110 provides the virtual reality access points 115a-b with a listing of the hosted virtual reality environments that the inmate may participate in. In certain embodiments, the virtual reality access points 115a-b may interface with the virtual control system 105 directly to determine the list of virtual reality environments hosted by the virtual reality server 110 that may be offered to the inmate. In that manner, the virtual reality access points 115a-b may be utilized to relieve the virtual reality server 110 of a portion of the administrative overhead that is required within a correctional setting in order to ensure that restrictions on inmate participation are enforced. In such embodiments, the virtual reality access points 115a-b relieves the virtual reality server 110 of enforcing rules regarding the virtual reality environment that each inmate is allowed to participate in and instead may utilize available resources on enforcing behavior restrictions within the running virtual reality environments.

In the illustrated embodiment, inmates in each of the groups 120a-b access virtual reality services by utilizing virtual reality headsets that are configured to interface with virtual reality access points 115a-b. The virtual reality headsets may interface with virtual reality access points 115a-b via wired or wireless connections. Each virtual reality access point 115a-b may be configured to only accept connections from certain inmate virtual reality headsets. In the embodiment of FIG. 1, the virtual reality headsets of inmates in group 120a are configured to interface with virtual reality access point 115a and the virtual reality headsets of inmates in group 120b are configured to interface with virtual reality access point 115b. Certain embodiments may utilize multiple virtual reality access points to support additional bandwidth. In such cases, the multiple virtual reality access points may be configured identically such that inmates can access virtual reality services at multiple virtual reality access point. The virtual reality headsets utilized by inmates may be configured such that a headset may be restricted for use with specific virtual reality access points, which in turn may be limited to providing virtual reality services that have been approved for inmates with a certain privilege status. For instance, in the illustrated embodiment, the headsets utilized by inmates in cells 120a are restricted for use with virtual reality access point 115a. However, virtual reality access point 115a may be configured to deny all request from inmates with a restricted privilege status.

Each of the virtual reality access points 115a-b are configured to provide inmates with access to virtual environments hosted by virtual reality server 110. In the illustrated embodiments, the provided virtual environments provided by the virtual reality server 110 include training and/or education scenarios 125, recreational activities 128, exercise and self-improvement routines 129 and counseling services 130. In other embodiments, the virtual reality server 110 may provide additional virtual environments. In some embodiments, separate virtual reality servers may be utilized to support each of the supported environments. For instance, a counseling server may be used to support virtual reality counseling environments. The virtual reality server 110 hosts virtual environments and allows authorized inmates to participate in one or more of these hosted virtual environments. The virtual reality server 110 also receives input from the user. These inputs may include, for example, control signals (e.g., restart a scenario) and movement data (e.g., changes in the direction of the user's gaze).

The virtual reality server 110 may simultaneously host one or more virtual environments. In the embodiment illustrated in FIG. 1, the virtual reality server 110 interoperates with the virtual reality control system 105 in order to determine and enforce applicable restrictions regarding the virtual environments that each inmate is authorized to participate in. In certain scenarios, inmates may be required to participate in virtual environments alone, that is without any other human participants. In other scenarios, inmates may be allowed to interact with other inmates within the same virtual environments. In certain embodiments, inmates may interact with prison staff and professional service providers via virtual worlds as part of training and education services 125 and/or counseling services 130 provided by the correctional facility. As described with respect to FIG. 2, in certain embodiments, inmates may be allowed to participate in visitation sessions via virtual environments hosted by the virtual reality server 110.

In certain embodiments, the virtual participants in virtual environments hosted by the virtual reality server 110 may be configured to provide training and education services 125 and/or counseling services 130. In certain embodiments, human participants may provide all or part of the training and education services 125 and/or counseling services 130 by interacting with inmates through the use of avatars. One or more inmates may be allowed to participate in a training, education or counseling service. In certain embodiments, certain inmates may be restricted to participating in such services alone, where such restrictions are determined based on privilege status information. For instance, inmates presently held in isolation within a correctional facility may likewise be restricted to participating alone within all provided virtual environments for all or part of the time the inmate is held in physical isolation. In such scenarios, reintroduction of an inmate held in isolation into the general population may be determined based in part based on an inmate's behavior within virtual environments that include other inmate participants.

The virtual reality control system 105 may be configured according to various embodiments, to implement security protocols and procedures pertaining the participation of inmates in virtual reality sessions. In certain embodiments, the virtual reality control system 105 may receive a request for a virtual reality session from an inmate housed in one of the cell groups 120a-b that supports virtual reality services. In certain embodiments, a request may be received from the virtual reality access point 115a-b that has allowed a connection from an inmate headset. In other embodiments, the request may be received from the virtual reality server 110. In certain embodiments, the virtual reality control system 105 may respond to an inmate's request by providing the inmate with a list of virtual reality programs that the inmate may run on the virtual reality server 110. In certain embodiments, the virtual reality control system 105 may instead respond to a request by providing the inmate with a list of virtual reality programs currently running on the virtual reality server 110 that the inmate is allowed to participate in. In order to provide this information, the virtual reality control system 105 may maintain a list of virtual reality programs currently running on the virtual reality server 110.

In each of these scenarios, virtual reality control system 105 may utilize information provided by the Facility Management System (FMS) 140 and the associated inmate database 145 in determining the virtual reality restrictions that are applicable to a particular inmate. In some embodiments, the FMS 140 and the inmate database 145 may be co-located within a controlled-environment facility. For instance, the FMS 140 and the inmate database 145 may be located within a correctional facility that houses the two groups of inmates 120a and 120b. In other embodiments, the FMS 140 and the inmate database 145 may be centrally and/or remotely located with respect to one or more controlled environment facilities.

In certain embodiments, the FMS 140 may be used to manage various types of information pertaining to one or more correctional facilities and the inmates that are housed therein. In certain embodiments, the FMS 140 may be used to track balance information for each inmate, such as balances for inmate trust accounts and balances for calling or other visitation accounts. In certain embodiments, the FMS 140 may be used to track schedule information for inmate, such as each inmate's trial schedule, including schedules for related hearings or other court appearances by an inmate. The FMS 140 may also be used to manage information related to each inmate's conviction and sentence, such as time served, time remaining to be served, and release date. The FMS 140 may also be used to manage information related to each inmate's criminal history and warnings. The FMS 140 may also be used to manage various types of logistical information such as cell and cellmate assignments, dietary restrictions, commissary order history and medical restrictions. The FMS 140 may also be used to track and manage information pertaining to visitations by each inmate including telephone call history and call recordings. The FMS 140 may also be used to track and manage information pertaining to known or suspected gang or criminal affiliations for each inmate and known or suspected affiliates of each inmate. The inmate database 145 may serve as a data repository for the inmate information that is managed and accessed via the FMS 140.

As described in additional detail with respect to FIG. 2, the FMS 140 may be used in enforcing restrictions on each inmate's visitation allowances, where these allowance are based in part on an inmate's privilege status classification. The FMS 140 of FIG. 2 may be similarly configured to determining applicable restrictions for each inmate's participation in provided virtual reality services. In certain embodiments, the FMS 140 may be used to store various rules that are used to enforce applicable security protocols and procedures. For instance, the FMS 140 may track an inmate's visitation allotment and deny any call attempts by the inmate once the visitation allotment has been depleted. As described, the privilege status classification of an inmate may indicate that additional privileges may be allowed to certain inmates. For instance, a trustee may be allotted additional monthly visitations and/or the use of additional forms of visitation, such as video visitations, or in the embodiment of FIG. 2, virtual reality visitations.

The FMS 140 may also be used in enforcing limits and restrictions on inmate participation in provided virtual reality sessions. In certain embodiments, the FMS 140 may be used to determine whether an inmate is currently eligible to participate in virtual reality sessions. In response to a request for a virtual reality session from an inmate, the virtual reality control system 105 may query the FMS 140 to determine the privilege status for the inmate. For instance, the FMS 140 may specify that visitation privileges for the inmate have been temporarily suspended for the requesting inmate. In another scenario, the FMS 140 may specify that the inmate is allowed the use of virtual reality services, but is limited to a certain duration (e.g., two hours a day). Based on such privilege status information provided by the FMS 140, the virtual reality control system 105 may respond to an inmate request with a denial or a approval of the request.

If an inmate is determined to be eligible to participate in virtual reality services, the virtual reality control system 105 may further utilize the privilege status information provided by the FMS 140 to determine the virtual environments that the requesting inmate may participate in. For instance, the FMS 140 may provide privilege status information specifying that an inmate has been restricted to isolation status. In such scenarios, the virtual reality control system 105 may restrict the requesting inmate to participate only in single participant virtual environments, or in virtual environments where all other participants are virtual participants controlled by the virtual reality software. The FMS 140 may likewise include privilege status information specifying that that inmate is not allowed contact with certain other inmates. The virtual reality control system 105 thus enforces such restriction by limiting the requesting inmate from environments where such blacklisted inmates are participating.

In certain embodiments, the privilege status information for an inmate may be further utilized by the virtual reality control system 105 to limit an inmate's participation within virtual reality sessions. In certain scenarios, based on the privilege status of the requesting inmate, the inmate may be limited to using avatars that may have functionality that is limited in various ways. For instance, an inmate that has certain privileges restricted may be limited to avatars that do not express facial emotions, may not use audio and/or do not have arms or means of gesticulating to other participants. In certain embodiments, an inmate with restricted privileges may be allowed to participate in virtual reality sessions with one or more other persons, but the virtual reality server 210 may enforce restrictions that limit the inmate to viewing pixelated representations of the avatars of other participants, thus limiting the ability of the inmate to interact with other participants.

In certain embodiments, the virtual reality control system 105 may specify limits on an inmate's virtual world participation based on the inmate's privilege status. For instance, an inmate with restricted privileges may be limited to avatars with buffer zones that prevent any contact with the avatars of other participants in the virtual reality session. Based on such restrictions, the virtual reality server 110 may allow the inmate to participate in a virtual reality session, but enforce such buffer zone limits that restrict the inmate's participation in the session. The virtual reality server 110 may likewise enforce privilege status restrictions that disable the use of certain sensors by an inmate, such as sensors used to detect inmate hand movement, thus limiting the inmate's participation in a hosted virtual environment.

FIG. 2 is a diagram illustrating certain components of a virtual reality system 200 that operates similarly to the embodiment of FIG. 1, but also provides inmates with virtual reality visitation sessions according to various embodiments. The system of FIG. 2 also includes the capabilities described with respect to FIG. 1 to provide a group of inmates in cells 220 with virtual reality services, such as training, education 225 and counseling 230 services that may include one or more human or computer-controlled virtual reality participants. These virtual reality services are run on virtual reality server 210 and are accessed by inmates via a virtual reality access point 215. As before, the virtual reality control system 205 is used to determine and enforce the applicable restrictions on an inmate's use of the virtual reality services.

In the embodiment of FIG. 2, the inmate may participate in virtual reality visitation sessions, where various aspects of these visitation sessions may be configured based on the privilege status of the inmate. In the illustrated embodiments, virtual reality visitation are scheduled via the visitation processing system 265. Requests for a virtual reality visitation may be received by the visitation processing system 265 from an inmate 220 or a prospective visitor 260 that is remote from the correctional facility that houses the inmate. Upon receiving the visitation request, the visitation processing system 265 may interoperate with the FMS 240 and the associated inmate database 245 in order to determine whether the requested visitation session with the remote visitor 260 can be authorized and further determine any restrictions on an inmate's participation in a virtual reality visitation session.

The FMS 240 may be used according to various embodiments to enforce restrictions on each inmate's use of the virtual reality visitation system. In particular, the FMS 240 may provide security protocol rules that may be applicable to all visitations by an inmate, including virtual reality visitations. For instance, in providing visitation services, visitation processing system 265 may limit an inmate's visitation sessions to sessions with visitors whose identities are listed in that inmate's Pre-Approved Contact (PAC) and/or Personal-Allowed Number (PAN) list. In some scenarios, the visitation processing system 265 may also enforce restrictions prohibiting an inmate from contacting certain individuals identified in a "do not contact" list. In various scenarios, the identity of a remote visitor 260 may be determined in part based on the phone number of the visitor, the device presented for use by the visitor, an email addresses or other account and/or password presented by the visitor. Each inmate's PAC, PAN, and/or do not contact list(s) may be stored in the inmate database 245 and accessed by the FMS 240 when determining the virtual reality environments that may be offered to the inmate. The inmate database 245 may also be used to store biometric information used to authenticate inmates and visitors prior to authorizing a visitation session. In addition to PAC, PAN, and/or do not contact list(s), FMS 240 may also store various other security profiles and rules that limit visitation sessions.

In certain embodiments, visitors 270 may only be allowed to participate in virtual reality visitations from within a visitation area provided and monitored by the correctional facility. In order to determine if a visitation from a monitored visitor 270 is authorized and the appropriate restrictions on an inmate's participation, the virtual reality server 255 may interface with the visitation processing system 265 to determine the inmate's privilege status and the attendant restrictions based on that status. The virtual reality visitation area may be co-located within the correctional facility or may be located remotely from the correctional facility. In either scenario, the physical actions of a visitor 270 may be monitored and recorded along with the virtual reality participation of the visitor. As with the training, education, and counseling virtual reality services described with respect to FIG. 1, each virtual reality visitation session may be recorded and stored in a repository 235. In the embodiment of FIG. 2, such recorded virtual reality sessions may be reviewed by investigators via an investigation module 250.

In certain embodiments, the investigation module 250 may include a virtual reality server that allows an investigator to retrieve and replay stored virtual reality sessions 235. In certain embodiments, an investigation may be triggered based on the detection of certain keywords or actions within a virtual realty session. For instance, the detection of certain gang-related keywords or hand signals within a hosted virtual reality visitation may trigger an investigation. In certain embodiments, the investigative module 250 may allow in investigator to review and search a transcript of the audio recorded during a virtual reality session. In the case of a virtual reality visitation or a multi-inmate virtual reality session, the investigation module 150 may allow an investigator to separately replay the audio and avatar participation from each of the individual participants.

In certain embodiments, the investigation module 250 may allow an investigator to utilize a virtual reality headset to view the stored virtual reality session from one or more perspectives. For instance, in certain embodiments, the investigation module 250 may allow an investigator to replay the actions of an inmate in a stored virtual reality session from the perspective of the inmate. The investigator may likewise utilize the investigation module 250 to replay all or part of a virtual reality session from the perspective of any one of the participants. In certain embodiments, the investigation module 250 may allow an investigator to replay a stored virtual reality session from one or more third party perspectives, such as the perspective of a virtual security camera position within the virtual reality environment.

Once a visitation is allowed between an inmate and a remote visitor 260 and/or monitored visitor 270, the participants may then be placed in a virtual reality environment hosted by virtual reality server 210. In the same manner as described with respect to the embodiment of FIG. 1, the virtual reality control system 205 may configure the virtual reality session based on the privilege status of the inmate 220. For instance, inmates with reduced privileges may be limited with regard to avatar selection and may be limited with regard to interactions with visitors. For instance, an inmate with restricted visitation privileges may have limited ability to use hand gestures or other body movement inputs. As described, the privilege status of an inmate may be used to enforce buffer zones around the inmate's avatar, thus preventing contact with the avatar of a visitor.

In certain embodiments, the privilege status of an inmate may limit the types of virtual reality visitation programs that are made available to the inmate by the virtual reality server 210. For instance, inmates may be initially restricted to virtual visitations that are conducted in a bare virtual visitation room. An inmate with greater privileges may be allowed to select from certain virtual visitation parameter settings, such as the selection of a venue. For instance, an inmate may be allowed to select a setting for a virtual visitation such as a bench in a virtual city park or a table in a virtual coffee shop. Additional privileges may allow inmates to further interact with visitors within the visitation programs, for instance by playing board games or other recreational activities.

FIG. 3 is a flowchart diagram providing certain steps of a process according to various embodiments, where the process provides an inmate of a correctional facility with available virtual reality services. The process of FIG. 3 begins at step 305 with the receipt of a request for virtual reality participation by an inmate. At step 310, a listing is determined of the virtual reality programs that are presently running at the virtual reality server that has received the inmate's participation request. In certain embodiments, all virtual reality programs currently running at all virtual reality servers that are available to the requesting inmate may also be determined at this time.

At step 315, based on the virtual reality restrictions pertaining to the requesting inmate and the virtual reality programs currently running at the virtual reality server, or other virtual reality programs available at other virtual reality servers accessible by the inmate, a listing of the virtual reality programs that are presently available to an inmate are determined. As described, this determination may entail querying the privilege status of the requesting inmate and, based on an inmate's privilege status, an inmate may be restricted to only limited participation in virtual reality scenarios. For instance, an inmate may have restricted privileges and may thus be limited to participating in virtual environments that have limited functionality. In certain scenarios, the privilege status of an inmate may prohibit the inmate from participation in all multi-person virtual reality sessions.

With the list of available virtual reality programs determined, at step 320, capacity for additional virtual reality programs is determined at the virtual reality server that has received the inmate's request. In certain embodiments, the capacity of other virtual reality servers that are accessible by the inmate may also be determined. If additional capacity is available, the inmate may be provided with the option of selection from joining a currently running virtual reality session or loading a new virtual reality session at the virtual reality server that received the inmate's request or another virtual reality server available to the inmate.

Based on the available capacity for new virtual reality programs, if any, and the available virtual reality environment that the inmate is authorized to utilize, at step 330, the inmate is offered a list of available virtual reality environment. At step 335, the inmate selects from the list of available virtual reality environment, which may include both presently running virtual reality sessions that the inmate is authorized to join and virtual reality environment that may be initialized and run on behalf of the inmate. At step 345, the inmate's selection is processed to determine whether the inmate has selected a currently running virtual reality or one that must be loaded and initialized. If the inmate selects a currently running virtual reality environment, at step 350, the inmate is allowed to join the ongoing virtual reality session. If the inmate selects a virtual reality environment that is not currently running, at step 360, the selected virtual reality environment is initialized on behalf of the inmate.

Referring back to the processing of an inmate's request for virtual reality services at step 320, if no additional capacity for an additional virtual reality program is determined to be available at the virtual reality server, or in some embodiments at all available reality servers, the inmate's other option is to join an ongoing virtual reality session. At step 325, whether the inmate can join an ongoing session is determined. In certain scenarios, the inmate may be authorized to use virtual reality programs that are currently running, but none of these virtual reality programs may have capacity for the inmate. Virtual reality programs may include limits on the numbers of participants, and as described, privilege status restrictions may prohibit more than one inmate in some virtual reality sessions. Other privilege status restrictions may prohibit all contact between certain inmates, thus potentially precluding certain inmates from joining certain ongoing sessions. If no options are present for the inmate to join an ongoing session, at step 340, the inmate is notified of a lack of capacity.

If capacity is present in one or more of the running virtual reality environments for which an inmate is authorized to participate, the inmate may be allowed to select from the available environments. At step 350, the inmate is allowed to join the ongoing virtual reality session. At step 355, applicable restrictions on inmate behavior in the virtual reality session are determined. As described, based on an inmate's privilege status, an inmate's participation in virtual reality sessions may be restricted, such as through the selection of avatars and the enforcement of buffer zones. Once the applicable restrictions have been determined and the virtual reality scenario has been configured in response to these restrictions, at step 365, the inmate's avatar is initialized and inserted into the virtual reality environment and the inmate's session begins.

FIG. 4 is a flowchart diagram providing certain steps of a process according to various embodiments for automatically terminating an inmate's virtual reality participation based on observed physical responses to the virtual reality session. The process of FIG. 4 begins at step 405 with the configuration of a virtual reality visitation session according the privilege status restrictions placed on an inmate. As described, these restrictions may limit the duration of the virtual visitation, such as due to a limited visitation allotment due to an infraction of a rule. In the scenarios, the privilege status of the inmate may limit the virtual visitation environment and the activities available within the virtual visitation environment. In other scenarios, the privilege status of the inmate may result in restrictions on the inmate's actions in the visitation such as through avatar selection or the use of buffer zones. Once the restrictions on the virtual visitation have been determined, the avatars for the inmate and the visitor have been initialized and inserted into the virtual environment and the visitation has begun, at step 410, the physiological response of the inmate may be monitored according to various embodiments.

In certain embodiments, the virtual reality headset used by the inmate may include one or more biometric sensors that are configured to monitor various physiological responses of the inmate. In certain embodiments, the one or more biometric sensors may be worn by the inmate in order to capture the inmate's physiological responses. In certain embodiments, these physiological responses of the inmate may be monitored via a biometric bracelet that is secured to the inmate, such as a wrist or ankle bracelet. In these various embodiments, the biometric data collected by these sensors may include physiological parameters such as heart rate, breathing rate, perspiration level and pupil dilation or other biometric data.

At step 415, the monitored physiological data may be utilized, but this use may depend on whether the inmate is participating in a counseling, training or educational virtual reality environments that is supported by the correctional facility. If the inmate is participating in one of these programs supported by the correctional facility, at step 420, certain of the monitored physiological responses of the inmate may be recorded. In certain embodiments, the counseling, training or educational virtual reality environments may include scenarios that are comprised of distinct events. For instance, an educational or training environment may include exercises to be completed by the inmate. Similarly, a counseling environment may expose the inmate to various scenarios, for instance environment and situations related to the inmate's drug and/or alcohol dependence. During such events, the physiological response of the inmate may be monitored and recorded.

If the inmate has previously completed or attempted a particular scenario, at step 425, the monitored physiological responses of the inmate may be compared to baselines established based on physiological data captured during the inmate's previous sessions. For instance, in the educational and training context, such comparisons of physiological responses may indicate abnormal behavior by the inmate and may be used as in indication that the inmate has mastered a particular skill or task. In the counseling context, monitoring physiological responses to certain triggers may be used to aid counselors in identifying progress or lack of progress by an inmate within a dependence treatment program.

Referring back to step 415, if the inmate is not participating in a training, education or counseling session, and is thus participating in a virtual reality visitation session or a recreational activity, the responses of the inmate may be further monitored. As step 430, the physiological responses of the inmate are compared against response thresholds that indicate a certain degree of agitation. If the responses of the inmate are within normal ranges or have deviated from normal only briefly (perhaps indicating surprise, but not agitation by the inmate), the physiological responses of the inmate will be further monitored at step 410. However, if the inmate's physiological response are determined to be outside of acceptable thresholds, at step 435, the inmate's virtual reality session may be terminated.

Similar to the various restrictions of virtual reality use and participation by an inmate that are determined based on the inmate's privilege status, the physiological thresholds used in step 430 may be configured based on the privilege status of each inmate. For instance, a trustee inmate may have this feature disabled or may have very high threshold settings that will not be easily triggered. Inmates with restricted privileges may have much lower thresholds. Inmates with a history of violence or outburst with particular visitors may have thresholds that are manually set to accommodate a particular situation or relationship between an inmate and a visitor. Using these thresholds, inmates may be allowed to participate in virtual reality environments but may have their session terminated if excited or agitated responses by the inmate are detected. In certain embodiments, inmates may be warned prior to termination of a session due to these threshold violations.

FIG. 5 is a block diagram of a virtual reality system 500 configured according to certain embodiments to support the described virtual reality control system and virtual reality server. In the illustrated embodiments, the virtual reality control system and virtual reality server are separate components. These components may be combined into a single virtual reality system 500 in certain embodiments. The virtual reality system 500 may include one or more processors 501. In various embodiments, communication processing system 500 may be a single-processor system including one processor 501, or a multi-processor system including two or more processors 501. Processor(s) 501 may include any processor capable of executing program instructions, such as an Intel Pentium™ series processor or any general-purpose or embedded processors implementing any of a variety of Instruction Set Architectures (ISAs), such as the x86, POWERPC®, ARM®, SPARC®, or MIPS® ISAs, or any other suitable ISA.

Virtual reality system 500 includes a chipset 502 that may include one or more integrated circuits that are connected to processor(s) 501. In certain embodiments, the chipset 502 may utilize a QPI (QuickPath Interconnect) bus 503 for communicating with the processor(s) 501. Chipset 502 provides the processor(s) 501 with access to a variety of resources. For instance, chipset 502 provides access to system memory 505 over memory bus 504. System memory 505 may be configured to store program instructions and/or data accessible by processors(s) 501. In various embodiments, system memory 505 may be implemented using any suitable memory technology, such as static RAM (SRAM), synchronous dynamic RAM (SDRAM), nonvolatile/Flash-type memory, or any other type of memory.

Chipset 502 may also provide access to a graphics processor 507. In certain embodiments, graphics processor 507 may be comprised within one or more video or graphics cards that have been installed as components of the communication processing system 500. Graphics processor 507 may be coupled to the chipset 502 via a graphics bus 506 such as provided by an AGP (Accelerated Graphics Port) bus or a PCIe (Peripheral Component Interconnect Express) bus. In certain embodiments, graphics processor 507 generates display signals and provides them to a display device 508 that may be coupled directly to the virtual reality system 500 or may be located remotely from the virtual reality system 500. In certain embodiments, the graphics process 507 may support display devices 508 that are virtual reality headsets worn by inmates and visitors participating in virtual reality sessions hosted by the system 500.

In certain embodiments, chipset 502 may also provide access to one or more user input devices 511. In such embodiments, chipset 502 may be coupled to a super I/O controller 510 that provides interfaces for a variety of user input devices 511, in particular lower bandwidth and low data rate devices. For instance, super I/O controller 510 may provide access to a keyboard and mouse or other peripheral input devices. In certain embodiments, super I/O controller 510 may be used to interface with coupled user input devices 511 such as keypads, biometric scanning devices, and voice or optical recognition devices. The user input devices 511 may interface with super I/O controller 510 through wired or wireless connections. In certain embodiments, the super I/O controller 510 may be coupled to the super I/O controller 510 via a Low Pin Count (LPC) bus 513.

Other resources may also be coupled to the processor(s) 501 of the virtual reality system 500 through the chipset 502. In certain embodiments, chipset 502 may be coupled to a network interface 509, such as provided by a Network Interface Controller (NIC) that is coupled to the virtual reality system 500. In certain embodiments, the network interface 509 may be coupled to the chipset 502 via a PCIe bus. According to various embodiments, network interface 509 may support communication via various wired and/or wireless networks. Chipset 502 may also provide access to one or more hard disk and/or solid state drives 515. In certain embodiments, the chipset 502 may also provide access to one or more optical drives 514 or other removable-media drives. Any or all of the drive devices 514 and 515 may be integral to the virtual reality system 500, or may be located remotely from the virtual reality system 500. In certain embodiments, the chipset 502 may also provide access to one or more Universal Serial Bus (USB) ports 516.

In various embodiments, a virtual reality system 500 does not include each of the components shown in FIG. 5. In various embodiments, a virtual reality system 500 may include various additional components in addition to those that are shown in FIG. 5. Furthermore, some components that are represented as separate components in FIG. 5 may in certain embodiments instead be integrated with other components. For example, in certain embodiments, all or a portion of the functionality provided by the illustrated components may instead be provided by components integrated into the one or more processor(s) 501 as a systems-on-a-chip.

The foregoing has outlined rather broadly the features and technical advantages of the present invention in order that the detailed description of the invention that follows may be better understood. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

What is claimed is:

1. A method for regulating the use of a plurality of supported virtual reality environments, each a computer generated virtual three-dimensional environment, by a plurality of residents of a controlled-environment facility, the method comprising:
receiving a request for a virtual reality session by a first resident of the plurality of residents of the controlled-environment facility;
determining one or more privilege status restrictions pertaining to the first resident;
determining, based on the privilege status restrictions, a list of virtual reality environments of the plurality of supported virtual reality environments that are allowed for the first resident, the privilege status restrictions restricting the first resident from certain of the plurality of supported virtual reality environments;
receiving a selection of a virtual reality environment from the first resident, the selection made by the first resident from the list of allowed virtual reality environments;
inserting a virtual reality avatar representing the first resident into the selected virtual reality environment and limiting functionality of the avatar within the selected virtual reality environment based on the determined privilege status restrictions, the avatar controlled within the selected virtual reality environment by the first resident; and
restricting the behavior of the avatar within the selected virtual reality environment based on the determined privilege status restrictions.

2. The method of claim 1, wherein the privilege status restrictions are based on the first resident's behavior in the controlled-environment facility.

3. The method of claim 1, wherein the list of available virtual reality environments includes a first virtual reality environment that is currently hosting a second resident of the plurality of residents.

4. The method of claim 3, wherein the determined privilege status restrictions prohibit the first resident from joining the first virtual reality environment based on the first virtual reality environment hosting the second resident.

5. The method of claim 4, wherein the determined privilege status restrictions prohibit the first resident from participating in virtual reality environments with other residents of the plurality of residents.

6. The method of claim 1, further comprising:
monitoring one or more physiological responses of the first resident while the first resident is controlling the avatar in the selected virtual reality environment.

7. The method of claim 6, further comprising:
assessing the first resident by comparing the one or more physiological responses of the first resident to prior physiological responses captured during prior participation of the first resident in the selected virtual reality environment.

8. The method of claim 6, further comprising:
warning the first resident if a physiological response of the one or more physiological responses exceeds a specified threshold.

9. The method of claim 8, wherein the specified threshold is determined based on the determined privilege status of the first resident.

10. The method of claim 1, wherein the list of virtual reality environments comprise a list of virtual reality programs currently running that are allowed for the first resident.

11. The method of claim 1, wherein limiting functionality of the avatar comprises limiting the avatar to not express facial emotions.

12. The method of claim 1, wherein limiting functionality of the avatar comprises limiting the avatar to not use audio.

13. The method of claim 1, wherein limiting functionality of the avatar comprises limiting the avatar to not have arms, or other means for gesticulating to other virtual reality environment participants.

14. The method of claim 1, further comprising limiting the first resident, based on the determined privilege status restrictions, to viewing pixelated representations of avatars of other participants in the selected virtual reality environment.

15. The method of claim 1, further comprising disabling operation of one or more virtual reality sensors with respect to the first resident, limiting the first resident's participation in the selected virtual reality environment, based on the determined privilege status restrictions.

16. The method of claim 1, further comprising preventing contact with avatars of other participants in the selected virtual reality environment, based on the determined privilege status restrictions, by implementing a buffer zone zone around the first resident avatar.

17. The method of claim 1, wherein the first resident is an inmate held in isolation within a correctional facility and the selected virtual reality environment includes other inmates, the method further comprising reintroducing the inmate into a general population of the correctional facility based at least in part on the inmate's behavior within the selected virtual reality environment.

18. A system for regulating the use of a plurality of supported virtual reality environments, each a computer generated virtual three-dimensional environment, by a plurality of residents of a controlled-environment facility, the system comprising:
- a virtual reality access point configured to receive a request for a virtual reality session by a first resident of the plurality of residents of the controlled-environment facility and further configured to receive a selected virtual reality environment from the first resident, the selection made by the first resident from a list of allowed virtual reality environments;
- a virtual reality control system configured to determine one or more privilege status restrictions pertaining to the first resident and further configured to determine, based on the privilege status restrictions, the list of virtual reality environments of the plurality of supported virtual reality environments that are allowed for the first resident, the privilege status restrictions restricting the first resident from certain of the plurality of supported virtual reality environments; and
- a virtual reality server configured to insert a virtual reality avatar representing the first resident into the selected virtual reality environment and limit functionality of the avatar within the selected virtual reality environment based on the determined privilege status restrictions, the avatar controlled within the selected virtual reality environment by the first resident and further configured to restrict the behavior of the avatar within the selected virtual reality environment based on the determined privilege status restrictions.

19. The system of claim 18, wherein the privilege status restrictions are based on the first resident's behavior in the controlled-environment facility.

20. The system of claim 18, wherein the list of available virtual reality environments includes a first virtual reality environment that is currently hosting a second resident of the plurality of residents.

21. The system of claim 20, wherein the determined privilege status restrictions prohibit the first resident from joining the first virtual reality environment based on the first virtual reality environment hosting the second resident.

22. The system of claim 21, wherein the determined privilege status restrictions prohibit the first resident from participating in virtual reality environments with other residents of the plurality of residents.

23. The system of claim 18, wherein the access point is further configured to receive inputs from one or more sensors configured to monitor one or more physiological responses of the first resident while the first resident is controlling the avatar in the selected virtual reality environment.

24. The system of claim 23, wherein the virtual reality control system is further configured to assess the first resident by comparing the one or more physiological responses of the first resident to prior physiological responses captured during prior participation of the first resident in the selected virtual reality environment.

25. The system of claim 23, wherein the virtual reality control system is further configured to warn the first resident if a physiological response of the one or more physiological responses exceeds a specified threshold.

26. The system of claim 25, wherein the specified threshold is determined based on the determined privilege status of the first resident.

27. The system of claim 18, wherein the virtual reality access point is further configured to only accept connections from certain inmate virtual reality headsets.

28. The system of claim 18, further comprising a virtual reality headset utilized by the first resident, the virtual reality headset configured to be restricted for use with only the virtual reality access point, based on the determined privilege status restrictions.

29. A method for a virtual reality visitation between a resident of a controlled-environment facility and a visitor, the method comprising:
- receiving a request for the virtual reality visitation session by the resident;
- determining one or more privilege status restrictions pertaining to the resident;
- determining, based on determined privilege status restrictions, a list of virtual visitation environments that are allowed for the resident;
- receiving a selection of a computer generated virtual three-dimensional visitation environment from the resident, the selection made by the resident from the list of allowed virtual visitation environments;
- inserting a computer generated virtual three-dimensional resident avatar representing the resident into the selected virtual visitation environment and limiting functionality of the avatar within the selected virtual visitation environment based on the determined privilege status restrictions, the resident avatar controlled within the selected virtual visitation environment by the resident;
- inserting a computer generated virtual three-dimensional visitor avatar representing the visitor into the selected virtual visitation environment, the visitor avatar controlled within the selected virtual visitation environment by the visitor; and
- restricting the behavior of the avatars within the selected virtual visitation environment based on the determined privilege status restrictions.

30. The method of claim 29, wherein the privilege status restrictions are based on the resident's behavior in the controlled-environment facility.

* * * * *

UNITED STATES PATENT AND TRADEMARK OFFICE
CERTIFICATE OF CORRECTION

PATENT NO. : 10,565,793 B2
APPLICATION NO. : 15/440273
DATED : February 18, 2020
INVENTOR(S) : Clements et al.

Page 1 of 1

It is certified that error appears in the above-identified patent and that said Letters Patent is hereby corrected as shown below:

In the Claims

In Column 18, Line 57, Claim 16, delete "buffer zone zone" and insert -- buffer zone -- therefor.

Signed and Sealed this
Seventeenth Day of March, 2020

Andrei Iancu
*Director of the United States Patent and Trademark Office*